(12) United States Patent  (10) Patent No.: US 7,637,741 B2
Devincenzo et al.  (45) Date of Patent: Dec. 29, 2009

(54) ORTHODONTIC ANCHOR

(75) Inventors: John Devincenzo, 1312 Garden St., San Luis Obispo, CA (US) 93401; Craig Jacobson, Encinitas, CA (US); Steven O. Luse, Vista, CA (US)

(73) Assignee: John DeVincenzo, San Luis Obispo, CA (US)

( * ) Notice: Subject to any disclaimer, the term of this patent is extended or adjusted under 35 U.S.C. 154(b) by 0 days.

(21) Appl. No.: 11/601,515

(22) Filed: Nov. 20, 2006

(65) Prior Publication Data

US 2008/0118885 A1 May 22, 2008

(51) Int. Cl.
*A61C 8/00* (2006.01)
(52) U.S. Cl. .......................................... 433/174; 433/18
(58) Field of Classification Search .................... 433/18, 433/173–174
See application file for complete search history.

(56) References Cited

U.S. PATENT DOCUMENTS

| | | | | |
|---|---|---|---|---|
| 4,639,219 A | * | 1/1987 | Gagin | 433/22 |
| 4,687,441 A | * | 8/1987 | Klepacki | 433/8 |
| 5,049,072 A | * | 9/1991 | Lueschen | 433/173 |
| 5,853,291 A | * | 12/1998 | DeVincenzo et al. | 433/18 |
| 6,203,323 B1 | * | 3/2001 | Beaty et al. | 433/173 |
| 6,354,834 B2 | * | 3/2002 | Kanomi et al. | 433/18 |
| 2002/0177103 A1 | * | 11/2002 | Pelak | 433/173 |
| 2004/0166460 A1 | * | 8/2004 | Devincenzo | 433/18 |
| 2006/0154205 A1 | * | 7/2006 | Reggie | 433/173 |

* cited by examiner

*Primary Examiner*—John J Wilson
*Assistant Examiner*—Heidi M Eide
(74) *Attorney, Agent, or Firm*—Rodgers & Rodgers

(57) ABSTRACT

An orthodontic implant comprised of one or two bony attachments, and, if there are two, one is smaller and affixed to the opposite end of the emerging portion, while the other utilizes a screw placed through an aperture. The smaller affixed portion is a tapered tac with the opposite emerging portion receiving an "O" ring removable cap onto which an adjustable rod can be contoured as needed after the implant has been affixed to bone.

6 Claims, 5 Drawing Sheets

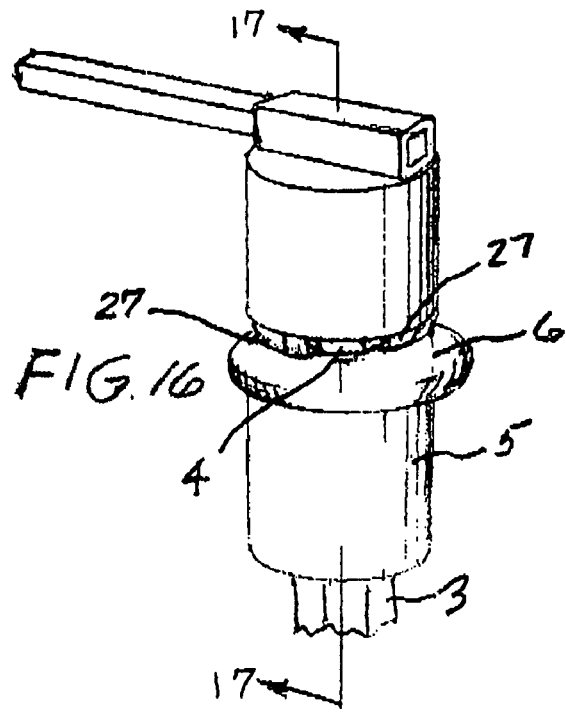
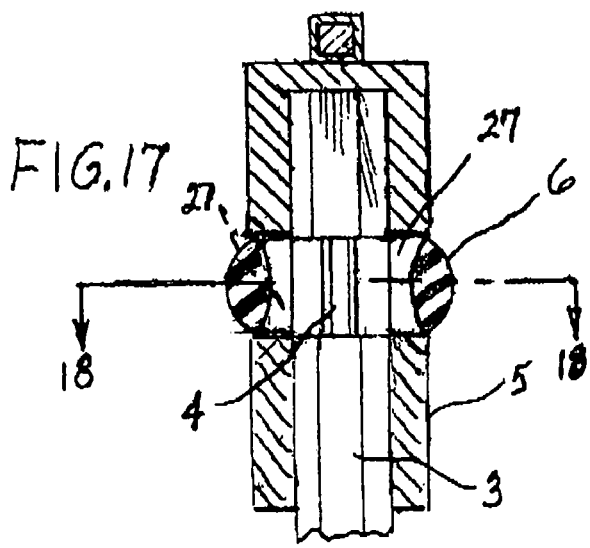
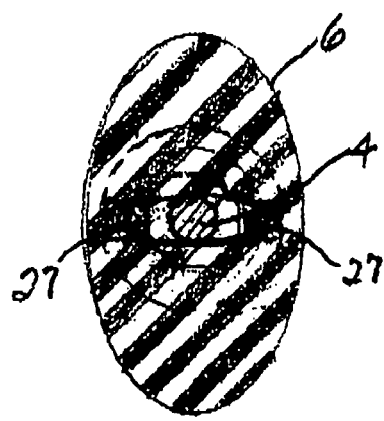

ORTHODONTIC ANCHOR

BACKGROUND OF THE INVENTION

Orthodontic implants have become increasingly popular in the past few years because of the need for absolute anchorage and the diminishing cooperation patients are exhibiting. Two basic types of implants are available, namely the single screw placed in the dentoalveolar bone between tooth roots and the skeletal miniplate attached to basal bone apical and away from the proximity of the roots.

The advantages of the single screw implant with a variety of head designs, depending on the manufacturer, include ease of placement, which can be performed by an orthodontist, and which is atraumatic and is less expensive. The disadvantages include possible root penetration, poor bony anchorage, limitation on the type of force vectors which can be utilized, bony insertion at an undesirable angle in order to avoid root damage, insertion more apically than desired so as to avoid root damage and the tendency to unscrew if the created moment tends to unwind the screw. Another disadvantage that frequently surfaces, particularly in the mandibular arch, is soft tissue proliferation at the emergence of the implant. The resultant hyperplastic tissue can sometimes completely engulf the exposed end making monthly adjustments difficult. By placing the implant emergence at or near the mucogingival junction, which is often difficult because of root proximity, this undesirable soft tissue response is avoidable.

The advantages of the multiscrew skeletal miniplate include better anchorage and hence larger magnitudes of force application, no or greatly reduced potential for root damage, better ability to withstand all forces in all directions and reduced chance of implant failure. The soft tissue response is much improved because emergence can approximate the mucogingival junction. The disadvantages include cost, more difficult placement and accompanying surgery and longer post-operative recovery. Placement will generally require the skills of an oral surgeon.

BRIEF SUMMARY OF THE INVENTION

The orthodontic implant according to this invention is designed for ease of insertion, adjustability of a wire or tube affixed to a cap which is held onto the emerging portion of the implant, fixation into bone at one or two separate locations, one of said fixations being a tapered tac over which a tool can be placed, and wherein a few light blows with a small hammer drive the tac a few millimeters into cortical bone. If only one fixation point is utilized, the tac is omitted. The second fixation point, if two penetrations are desired, is located more apically and hence reducing the danger of root damage, is home to a large diameter and longer bony screw which is inserted through the appropriately sized aperture.

The cap being internally angular, as is the emerging portion of the anchor, can be rotated in a number of directions hence changing the location and direction of the wire or tube permanently affixed thereto. The cap is easily removed from the implant thus affording the practitioner the ability to modify the length and configuration of the attached or emerging wire while the cap is securely maintained by an "O" ring fitting into a groove within the implant head.

A special sliding tube fits onto the arch wire thus permitting the clinician to stabilize the sliding tube wherever desired and then deliver forces directly along the archwire if so desired.

BRIEF DESCRIPTION OF THE SEVERAL VIEWS OF THE DRAWINGS

FIG. 16 is an enlarged perspective view showing another modification of the anchor;

FIG. 17 is a cross-sectional view taken along the line 17-17 in FIG. 16; and

FIG. 18 is a cross-sectional view taken along the line 18-18 in FIG. 17.

DETAILED DESCRIPTION OF THE INVENTION

Figure 1:
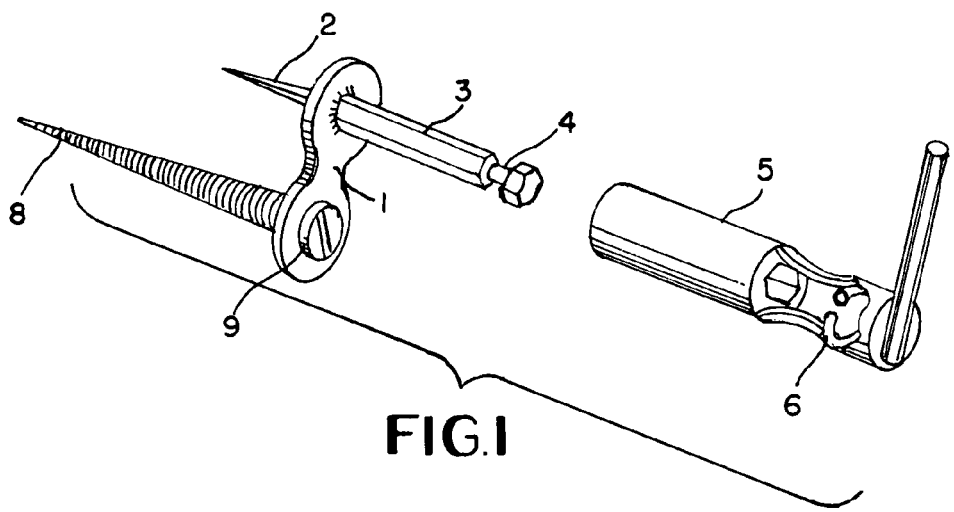
FIG. 1 is a perspective view of an orthodontic anchor in accordance with this invention.

In accordance with this invention, the orthodontic anchor or implant is viewed in FIG. 1 and comprises plate 1 which is a thin sheet of biocompatible material such as titanium through which at its more occlusal opening a shaft of material is inserted and attached thereto which has at its bony surface side a tapered, grooved, short tac 2 which can penetrate the dense, outer layer of cortical bone. Tac 2 is about 3 mm in length and about 1.4 mm in diameter at its widest dimension. Emerging from the gingival side of the body is angular head 3 with groove 4 located near its distal end. Fitting over angular head 3 is cap 5 which is also internally angular so as to fit snugly over angular head 3. An "O" ring 6 is contained within cap 5 by a groove formed on the inner surface of cap 5 such that when cap 5 is pressed onto angular head 3 the "O" ring locks into groove 4 in angular head 3. An extension wire 7 is either attached to the top of cap 5 directly or extends from an appropriately sized angular tube which has been attached to the cap. This extension wire permits the clinician to adjust the wire into a number of configurations and locations. Likewise by rotating cap 5 before placement on angular head 3, the position of extension wire 7 can be varied. Also, major anchor screw 8 is inserted through an appropriately sized orifice 9 formed in plate 1 and screwed deeper into the bone after tac 2 has been used to position and stabilize plate 1. Major anchor screw 8 is similar in size to a conventional single screw implant and is approximately 5-7 mm in length and 1.7-2.2 mm in diameter at its largest dimension.

Figure 2A:
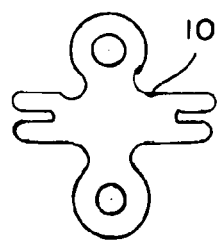
FIGS. 2A, 2B and 2C are top plan views of modified designs of the plate element of the anchor.
Figure 2B:
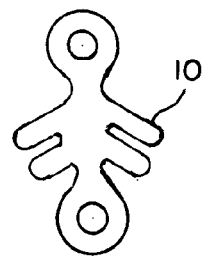
Figure 2C:
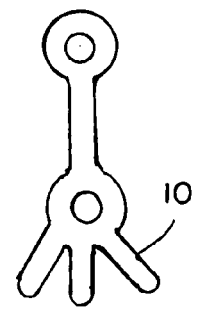

FIGS. 2A, 2B and 2C show modifications to plate 1 such that thin, bendable projections 10 are added for additional stabilization by utilizing osseointegration on, around and over these thin projections.

Figure 3:
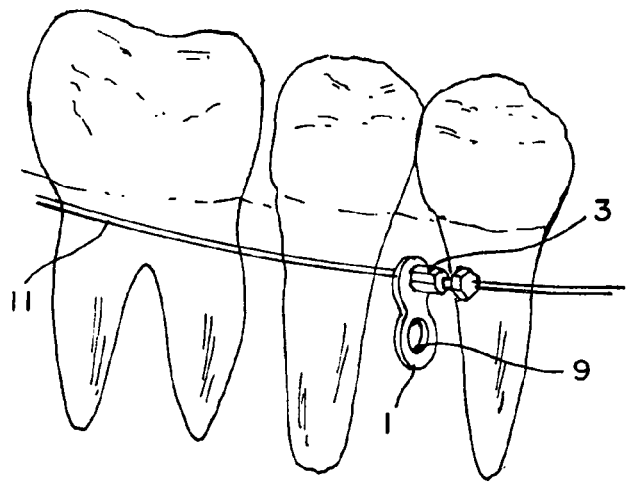
FIG. 3 is a perspective view showing placement of the anchor.

FIG. 3 depicts three mandibular posterior teeth with plate 1 placed such that head 3 is emerging at the mucogingival junction 11 with larger orifice 9 located more apically where there is greater distance between the roots.

Figure 4:
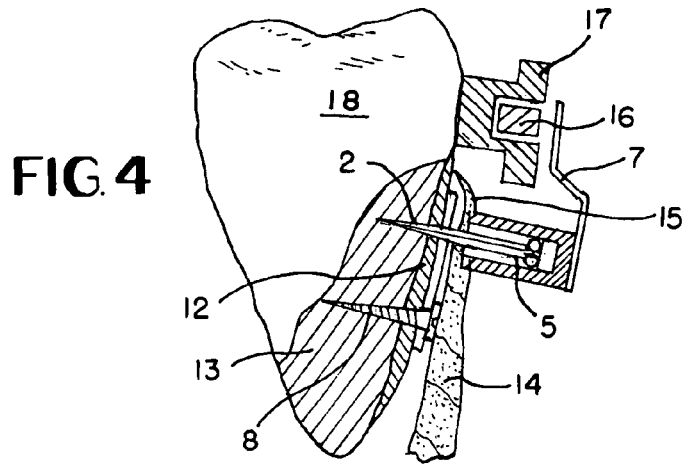
FIG. 4 is a side elevational view with a cross-sectional view of the anchor.
Figure 4A:
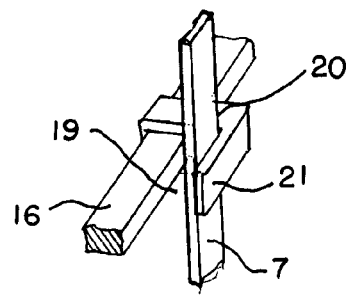
FIG. 4A is an enlarged perspective view of a portion of the anchor.

FIGS. 4 and 4A show all aspects of the implant according to this invention. A layer of dense cortical bone 12 is penetrated by both tac 2 and screw 8 while looser medulary bone 13 is pierced primarily by screw 8. The implant is placed under soft tissue periostium 14 while cap 5 enters slightly into the soft overlying gingival connective tissue 15. Archwire 16 is contained within bracket 17 which is in turn attached to the buccal surface of a tooth 18. As shown in FIG. 4A, contoured extension wire 7 fits into an opening 19 on sliding tube 20 and is stabilized laterally by projection 21 which extends therefrom.

Figure 5:
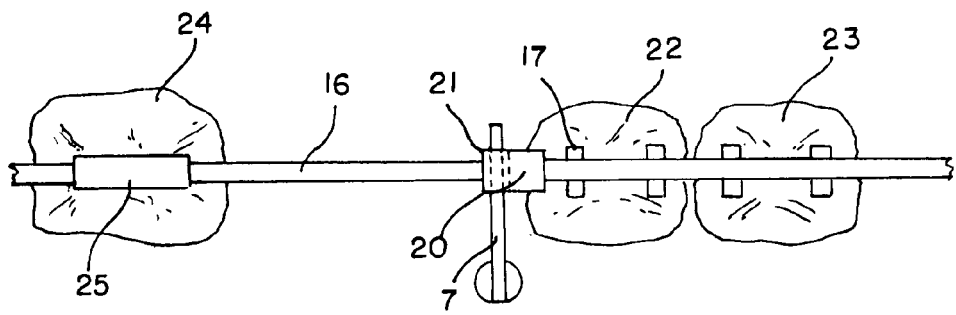
FIGS. 5, 6, 7 and 8 show operation of the anchor in connection with an archwire.

FIG. 5 is a buccal view of a clinical situation in which it is desirable to stabilize the more anterior teeth while moving the molar towards them. Sliding tube 20 fits onto the archwire 16 and is pressed against bracket 17 by extension wire 7 held against archwire 16 by projection 21. A force can then be applied from bicuspid tooth 22 or cuspid tooth 23 to molar tooth 24 thereby permitting the molar tooth to slide on archwire 16 through its own buccal tube 25.

Figure 6:
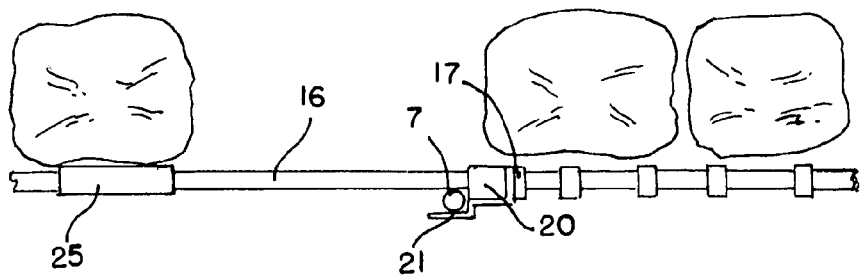

FIG. 6 is an occlusal view of the same scenario with archwire 16 extending through molar buccal tube 25 and onto which sliding tube 20, with its stabilizing projection 21, help contain extension wire 7. Sliding tube 20 is held firmly against bracket 17 by extension wire 7. Extension wire 7 is also attachable to archwire 16 by other known tubes, brackets and attachment wires.

Figure 7:
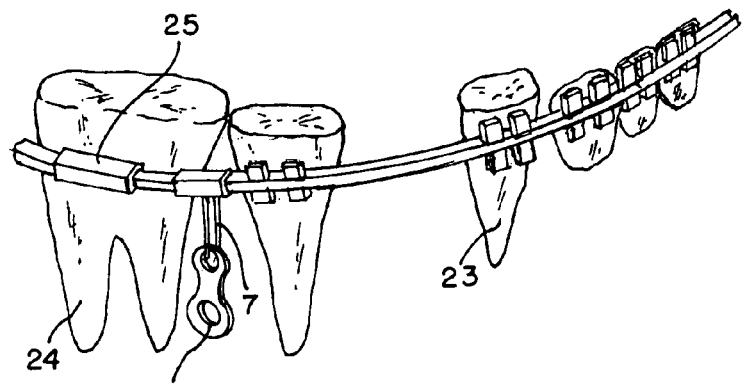

FIG. 7 is a buccal view of a clinical situation in which it is desirable to stabilize the more posterior molar 24, while retracting the anterior teeth including the cuspid 23. The extension wire 7 presses the sliding tube against molar buccal tube 25, thereby preventing molar mesial movement while retracting the anterior teeth into the extraction site.

Figure 8:
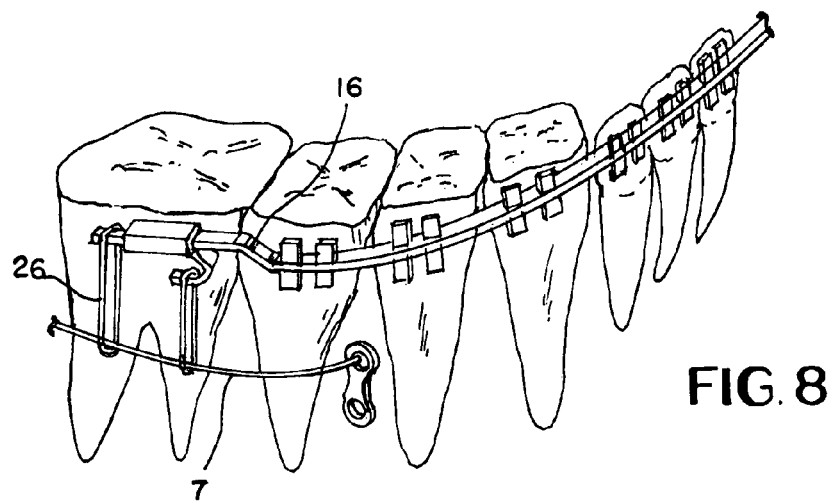

FIG. 8 shows an extruded molar and the insertion of cap 5 at a rotation resulting in extension wire 7 being approximately parallel to archwire 16 rather than perpendicular to the archwire as depicted in FIGS. 5-7. With extension wire 7 in this location, vertical forces 26 can be positioned anywhere along extension wire 7 to direct the desired intrusion force.

Figure 9:
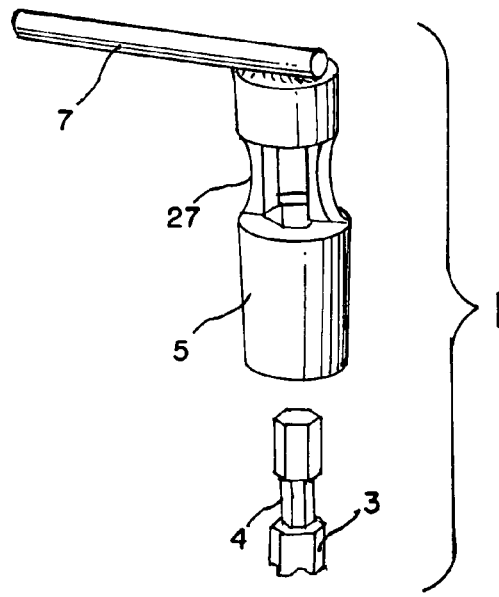
FIG. 9 is a partial exploded view of a modification of the anchor.
Figure 10A:
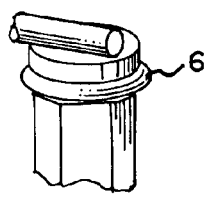
FIGS. 10A, 10B and 10C depict different applications of the anchor "O" ring.
Figure 10B:
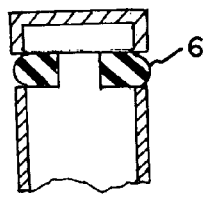
Figure 10C:

FIGS. 9, 10A, 10B and 10C show a modification to the "O" ring-cap retention mechanism in that the "O" ring fits on the outside of cap 5 rather than inside cap 5 with the cap modified to only contain, in the "O" ring region, two contoured pillars 27. An elliptically shaped "O" ring shown in FIG. 10C, thicker in its short axis and thinner in its long axis, encircles cap 5 and is held in place by inwardly bowed pillars 27 which interconnect two separate sections of cap 5, as shown in FIG. 9. The thicker sections of the "O" ring would extend into groove 4.

Figure 11:
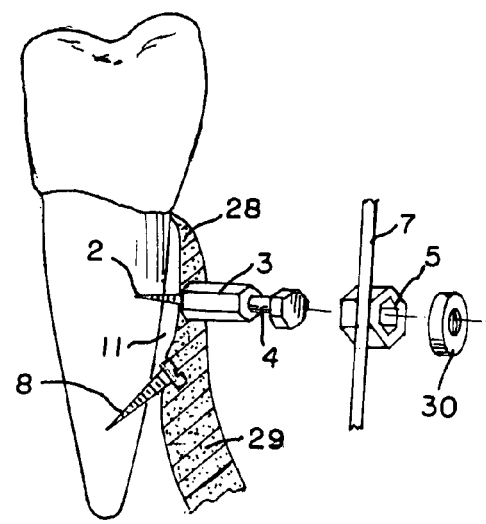
FIG. 11 is a perspective view of a modification of the implant.

FIG. 11 is similar to FIG. 4 and shows a different head extending through the gingival mucosa. Occlusally to the head is attached gingival 28 while apically to the head is loose connective tissue 29. The tapered implant 2 is inserted at the mucogingival junction 11. The extruding portion of the implant, as depicted in FIG. 11, is a modification of that described in FIG. 1 in that cap 5 is open at both ends and is positioned below groove 4 and "O" ring 30 fills groove 4. "O" ring 30 is larger in diameter than the outer dimension of cap 5 thereby preventing the displacement of cap 5.

Figure 12:
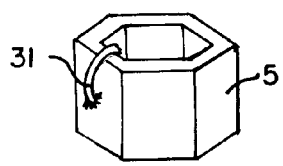
FIGS. 12, 13 and 14 show modified versions of the cap securing means.
Figure 13:
Figure 14:
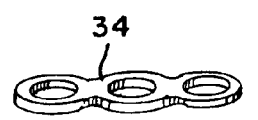

FIGS. 12, 13 and 14 show three additional ways cap 5 is secured to the extruded portion of the implant. In FIG. 12, flexible wire 31 is permanently attached to cap 5 at one end while free to move at the other end. The spring action of the wire keeps cap 5 affixed to the anchor head by engaging in groove 4. In FIG. 13, a flexible ring is inserted into groove 4 and is removed at will by inserting an instrument into the small portion 32. In FIG. 14, hooks 33 are an integral part of cap 5 and an elastomeric chain 34 is attached from hook to hook with the center hole fitting around shaft 3 and resting in groove 4.

Figure 15:
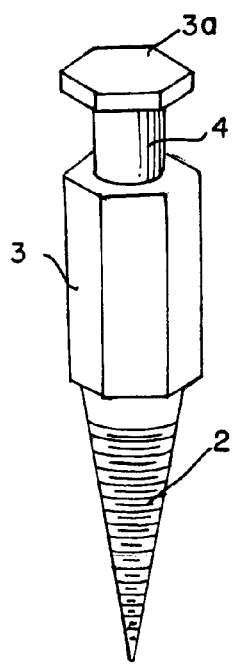
FIG. 15 is an elevational view of a further modification of the anchor.

FIG. 15 depicts a single anchor without plate 1 designed to be inserted singularly into bone and with a protruding head and cap as shown in FIGS. 11-14. The anchor includes bony screw portion 2, long angular shafts 3, short groove 4 and small angular portion 3a. A cap, as shown in FIGS. 12 and 14, fits over long angular shaft 3. An "O" ring disposed in groove 4 or one of the attaching means of FIGS. 5, 12, 13 or 14 are adaptable to secure the cap in place.

The invention claimed is:

1. An orthodontic anchor comprising a tac for piercing bone, an anchor screw spaced from said tack and for piercing bone more deeply than said tac, the diameter of said anchor screw being greater than the diameter of said tac, said tac and said anchor screw interconnected by a flat plate, said flat plate being rotatable with the axis of said tac being the center of rotation, the end of the tac that will project from said bone in use includes an elongated angular multi-sided orthodontic attachment head, a cap enveloping said orthodontic attachment head, said cap being formed of upper and lower sections interconnected by means of a pair of inwardly bowed pillars, the shortest distance between said pillars being greater than the distance between opposing sides of said orthodontic attachment head, an "O" ring extending around said pillars, said "O" ring being thicker along one axis than the axis disposed perpendicular thereto, said thicker portions of said O-ring being disposed intermediate said pillars, a groove formed in said orthodontic attachment head, and said thicker sections being disposed in said groove to hold said cap in place.

2. An orthodontic anchor according to claim 1 wherein an extension wire is removably secured to said cap at one end and to an archwire at the other end.

3. An orthodontic anchor according to claim 2 wherein said extension wire extends from said cap omnidirectionally.

4. An orthodontic anchor according to claim 2 wherein said extension wire is secured to said archwire by means of a sliding tube.

5. An orthodontic anchor according to claim 4 wherein a projection extends from said sliding tube and said extension wire is attached to said projection.

6. An orthodontic anchor according to claim 1 wherein an angular tube is secured to said cap.

* * * * *